(12) United States Patent
Cooke et al.

(10) Patent No.: US 7,390,821 B2
(45) Date of Patent: *Jun. 24, 2008

(54) METHODS OF REDUCING ANGIOGENESIS

(75) Inventors: John Cooke, Palo Alto, CA (US); Christopher Heeschen, Frankfurt (DE); Michael Weis, Munich (DE)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/366,163

(22) Filed: Mar. 1, 2006

(65) Prior Publication Data

US 2006/0148675 A1    Jul. 6, 2006

Related U.S. Application Data

(63) Continuation of application No. 10/358,370, filed on Feb. 3, 2003, now Pat. No. 7,045,534.

(60) Provisional application No. 60/356,687, filed on Feb. 12, 2002.

(51) Int. Cl.
| A61K 31/445 | (2006.01) |
| A61K 31/415 | (2006.01) |
| A61K 31/40 | (2006.01) |
| A61K 31/235 | (2006.01) |
| A61K 31/14 | (2006.01) |

(52) U.S. Cl. .................. 514/315; 514/386; 514/408; 514/410; 514/416; 514/533; 514/642; 514/659

(58) Field of Classification Search .................. None
See application file for complete search history.

(56) References Cited

U.S. PATENT DOCUMENTS

| 4,503,038 | A | * | 3/1985 | Banda et al. | 424/537 |
| 4,749,686 | A | | 6/1988 | Hintze | |
| 4,966,890 | A | * | 10/1990 | Gillespie | 514/25 |
| 5,069,904 | A | | 12/1991 | Masterson | |
| 5,318,957 | A | | 6/1994 | Cid et al. | |
| 5,686,448 | A | | 11/1997 | Baldone | |
| 5,820,583 | A | | 10/1998 | Demopulos et al. | |
| 5,932,545 | A | * | 8/1999 | Henkin et al. | 514/13 |
| 6,034,079 | A | * | 3/2000 | Sanberg et al. | 514/225.8 |
| 6,121,289 | A | | 9/2000 | Houdi | |
| 6,261,279 | B1 | | 7/2001 | Demopulos et al. | |
| 6,417,205 | B1 | | 7/2002 | Cooke et al. | |
| 6,610,713 | B2 | | 8/2003 | Tracey | |
| 6,734,215 | B2 | | 5/2004 | Shytle et al. | |
| 6,838,471 | B2 | | 1/2005 | Tracey | |
| 7,045,534 | B2 | * | 5/2006 | Cooke et al. | 514/315 |
| 2002/0016344 | A1 | | 2/2002 | Tracey | |
| 2002/0016370 | A1 | | 2/2002 | Shytle et al. | |
| 2002/0016371 | A1 | | 2/2002 | Shytle et al. | |
| 2002/0028798 | A1 | | 3/2002 | Demopulos et al. | |
| 2002/0054896 | A1 | | 5/2002 | Studin | |
| 2003/0087962 | A1 | | 5/2003 | Demopulos et al. | |
| 2003/0096807 | A1 | | 5/2003 | Demopulos et al. | |
| 2003/0096831 | A1 | | 5/2003 | Stone et al. | |
| 2003/0130165 | A1 | | 7/2003 | Reitz et al. | |
| 2003/0158112 | A1 | | 8/2003 | Campochiaro | |
| 2003/0235589 | A1 | | 12/2003 | Demopulos et al. | |
| 2004/0044083 | A1 | | 3/2004 | Shytle et al. | |
| 2004/0132737 | A1 | | 7/2004 | Cormier et al. | |
| 2004/0204355 | A1 | | 10/2004 | Tracey et al. | |
| 2005/0021092 | A1 | | 1/2005 | Yun et al. | |
| 2005/0075702 | A1 | | 4/2005 | Shafer | |

FOREIGN PATENT DOCUMENTS

| WO | WO 00/35279 | 6/2000 |
| WO | WO 00/35279 A1 | 6/2000 |
| WO | WO 00/35280 | 6/2000 |
| WO | WO 01/08684 | 2/2001 |

OTHER PUBLICATIONS

Hannan, Robert L. et al. "Endothelial cells synthesize basic fibroblast growth factor and transforming growth factor beta", Growth Factors, 1998, vol. 1, pp. 7-17.

Edelmen, Elazer R. et al."Basic Fibroblast Growth Factor Enhances the Coupling of Intimal Hyperplasia and Proliferation of Vasa Vasorum in Injured Rat Arteries", J. Clin. Invest., vol. 89, Feb. 1992, pp. 465-473.

Ribatti, Domenico et al. "Human Neuroblastoma Cells Produce Extracellular Matrix-Degrading Enzymes, Induce Endothelial Cell Proliferation and are Angiogenic In Vivo", Int. J. Cancer: 77, 449-454 (1998).

Hyman, Ph.D., Leslie et al. "Hypertension, Cardiovascular Disease, and Age-Related Macular Degeneration" Arch Opthamol, vol. 118, Mar. 2000.

Cancer, Principles & Practice of Oncology, 6th ed. Published by Lippiincott Williams & Wilkins (PA), 2001 pp. 143-145, 510.

Harrison's Principles of Internal Medicine, vol. 2, Isselbacher et al. eds., published 1994 by McGraw-Hill, Inc. (NY), pp. 1994-1995.

(Continued)

*Primary Examiner*—Raymond J. Henley, III
(74) *Attorney, Agent, or Firm*—Paula A. Borden; Carol L. Francis; Bozicevic, Field & Francis LLP

(57) ABSTRACT

The present invention provides methods of reducing angiogenesis in an individual. The methods generally involve administering to the individual an effective amount of a nicotinic acetyl choline receptor antagonist. The methods are useful to treat conditions associated with or resulting from angiogenesis, particularly pathological angiogenesis. The invention further provides methods of treating a condition associated with or resulting from angiogenesis.

49 Claims, 5 Drawing Sheets

OTHER PUBLICATIONS

L.E. Chavez-Noriega et al. "Characterization of the recombinant human neuronal nicotinic acetylcholine receptors alpha3beta2 and alpha4beta2 stably expressed in HEK293 cells" Neuropharmacology, date unavailable.
B.T. Hawkins et al. "Smoking and ischemic stroke: a role for nicotine?" Trends in Pharmacological Sciences, vol. 23, No. 2, Feb. 1, 2002, pp. 78-82.
Schuller et al. (1989) *Carcinogenesis* 10:1753-1755.
Maneckjee et al. (1994) *Cell Growth Differ.* 5:1033-1040.
Hong et al. (1995) *J. Pharm. Sci.* 84:65-70.
Schuller et al. (1989) *Biochem. Pharmacol.* 38:3439-3442.
Yancopoulos et al. (1998) *Cell* 93:661-4.
Folkman et al. (1996) *Cell* 87;1153-5.
Hanahan et al. (1996) *Cell* 86:353-64.
Carmeliet et al. (2000) *Nature* 407:249-257.
Folkman (1995) *Nat Med* 1:27-31.
Heeschen et al. (2001) *Nat Med* 7:833-837.
Grando et al. (1995) *J Invest Dermatol* 105:774-781.
Macklin et al. (1998) *Pharmacol Exp Ther* 287:435-439.
Wessler et al. (1999) *Clin Exp Pharmacol Physiol* 26:198-205.
Kawashima et al. (1989) *Neurosci Lett* 104:336-339.
Kawashima et al. (1990) *Neurosci Lett* 119:156-158.
Kureishi et al. (2000) *Nat Med* 6:1004-1010.
Jang et al. (2000) *Circulation* 102:1414-1419.
Couffinhal et al. (1998) *Am J Pathol* 152:1667-1679.
Lagasse and Weissman (1996) *J Immunol Methods* 197:139-150.
Villablanca (1998) *J Appl Physiol* 84:2089-2098.
Tarroni, P. et al. "Neuronal-type nicotinic receptors in human neorblstoma and small-cell lung carcinoma cell lines" FEBS Lett., 312: 66-70, 1992.
Cunningham, J.M. et al., Acetycholine receptors in small cell carcinomas, J. Neurochem., 45: 159-167, 1985.
Quik, M. et al., a-Bungaroxotin blocks the nicotinic receptor mediated increase in cell number in a neuroendocrine cell line. Brain Res., 655: 161-167, 1994.
Schuller et al. Nicotine, acetylcholine and bombesin are trophic growth factors in neuroendocrine cell line. Brain res., 655: 161-167, 1994.
Fucile et al. "Cholinergic stimulation of human micro-cytoma cell line H69" Biochem. Biophys. Res. Commun., 230: 501-504, 1997.
Novak et al., "Nicotine effects of proliferation and the bombesin-like peptide autorcine system in human small cell ling carcinoma SHP77 cells in culture" Lung Cancer, 29: 1-20, 2000.
Codignola, A., et al. "Serotonin release and cell profliferation are under the control of a-bungarotoxin-sensitive nicotinic receptors in small-cell lung carcinoma cell lines" FEBS Lett., 342:286-290, 1990.
Williams, C.L. and Lennon, V.A. Activation of M3 muscarinic acetylcholine receptors inhibits voltage-dependent calcium influx in small cell lung carcinoma cell. J. Biol. Chem., 265: 1443-1447, 1990.
Maneckjee, R. and Minna J.D., Opioid and nicotine receptors affect growth regulation of human lung cancer cell lines. Proc Natl. Acad. Sci. USA, 87: 3294-3298, date unavailable.

Song et al., Acetylcholine is Synthesized by and Acts as an Autocrine Growth Factor for Small Cell Lung Carcinoma, Cancer Research 63, 214-221, Jan. 1, 2003.
Heeschen, C. et al. "A novel angiogenic pathway mediated by non-neuronal nicotinic acetylcholine receptors", Journal of Clinical Investigation, New York, NY, US, vol. 110, No. 4, Aug. 2002, pp. 527-536.
Heeschen C. et al. "Nicotine Stimulates Angiogenesis and Promotes Tumor Growth and Atherosclerosis" Nature Medicine, Nature Publishing, CO, US, Col. 7, No. 7, Jul. 2001, pp. 833-839.
A.C. Villablanca "Nicotine Stimulates DNA Synthesis and Proliferation in Vascular Endothelial Cells in Vitro" Journal of Applied Physiology, vol. 84, No. 6, 1998, pp. 2089-2098.
Maneckjee, R. et al., "Effects of opioids and nicotine on apoptosis in human lung cancer cells" Analgesia (1995) 1 (4-6), 548-52.
Jacobi J. et al. "Nicotine Accelerates Angiogenesis and Wound Healing in Genetically Diabetic Mice" in The American Journal of Pathology. Jul. 2002 vol. 161, nr 1, pp. 97-104.
Takamura et al. "Effects of Various Chemical Compounds of Ehrlich Ascites Tumor Cells in a Maintenance Medium", 1989, vol. 14, Nr. 2, pp. 241-245.
Stone et al., "Effects of Nicotinic Antagonists on Ocular Growth and Experimental Myopia", Investigative Ophthalmology & Visual Science, Mar. 2001, vol. 42, No. 3, pp. 557-565.
Stone et al., "Associations between Childhood Refraction and Parental Smoking", Investigative Ophthalmology & Visual Science, Oct. 2006, vol. 47, No. 10, pp. 4277-4287.
Chavez-Noriega et al., "Characterization of the recombinant human neuronal nicotinic acetylcholine receptors $\alpha 3\beta 2$ and $\alpha 4\beta 2$ stably expressed in HEK293 cells", (2000), Neuropharmacology, vol. 39, pp. 2543-2560, XP-002315250.
Hawkins et al., Smoking and ischemic stroke: a role for nicotine?: (2002), Trends in Pharmacological Sciences, vol. 23, No. 2, pp. 78-82, XP-002315249.
Heeschen et al., "Nicotine stimulates angiogensis and promotes tumor growth and atherosclerosis", (2001), Nature Medicine, vol. 7, No. 7, pp. 833-839, XPO08040638.
Heeschen et al., "A novel angiogenic pathway mediated by non-neuronal nicotinic acetylcholine receptors", (2002), The Journal of Clinical Investigation, vol. 110, No. 4, pp. 527-536, XP-002279081.
Jacobi et al., "Nicotine Accelerates Angiogensis and Wound Healing in Genetically Diabetic Mice", (2002), American Journal of Pathology, vol. 161, No. 1, pp. 97-104, XP-008065321.
Maneckjee et al., "Effects of opiods and nicotine on apoptaosis in human lung cancer cells", (1995), Analgesia, vol. 1(4-6), pp. 548-552, XP8065326.
Takamura et al., "Effects of Various Chemical Compounds on Ehrlich Ascites Tumor Cells in a Maintenance Medium", (1989), vol. 14, pp. 241-245.
Villablanca, "Nicotine stimulates DNA synthesis and proliferation in vascular endothelial cells in vitro", (1998), Journal of Applied Physiology, vol. 84, No. 6, pp. 2089-2098, XP-002315260.

\* cited by examiner

Expression of nAChR in ischemic hind limbs

METHODS OF REDUCING ANGIOGENESIS

CROSS-REFERENCE

This application is a continuation of U.S. patent application Ser. No. 10/358,370, filed Feb. 3, 2003, now U.S. Pat. No. 7,045,534, which claims the benefit of U.S. Provisional Patent Application No. 60/356,687 filed Feb. 12, 2002, which applications are incorporated herein by reference in their entirety.

STATEMENT REGARDING FEDERALLY SPONSORED RESEARCH

This invention was made with government support under grant nos. R01 HL-58638 awarded by the National Heart, Lung and Blood Institute, and the Tobacco-Related Research Disease Program of the State of California. The government may have certain rights in this invention.

FIELD OF THE INVENTION

The invention relates generally to the field of regulation of angiogenesis and vasculogenesis, particularly to reduction of pathological angiogenesis.

BACKGROUND OF THE INVENTION

Angiogenesis and vasculogenesis are processes involved in the growth of blood vessels. Angiogenesis is the process by which new blood vessels are formed from extant capillaries, while vasculogenesis involves the growth of vessels deriving from endothelial progenitor cells. Angiogenesis is a complex, combinatorial process that is regulated by a balance between pro- and anti-angiogenic molecules. Angiogenic stimuli (e.g. hypoxia or inflammatory cytokines) result in the induced expression and release of angiogenic growth factors such as vascular endothelial growth factor (VEGF) or fibroblast growth factor (FGF). These growth factors stimulate endothelial cells (EC) in the existing vasculature to proliferate and migrate through the tissue to form new endothelialized channels.

Angiogenesis and vasculogenesis, and the factors that regulate these processes, are important in embryonic development, inflammation, and wound healing, and also contribute to pathologic conditions such as tumor growth, diabetic retinopathy, rheumatoid arthritis, and chronic inflammatory diseases (see, e.g., U.S. Pat. No. 5,318,957; Yancopoulos et al. (1998) *Cell* 93:661-4; Folkman et al. (1996) *Cell* 87; 1153-5; and Hanahan et al. (1996) *Cell* 86:353-64).

Both angiogenesis and vasculogenesis involve the proliferation of endothelial cells. Endothelial cells line the walls of blood vessels; capillaries are comprised almost entirely of endothelial cells. The angiogenic process involves not only increased endothelial cell proliferation, but also comprises a cascade of additional events, including protease secretion by endothelial cells, degradation of the basement membrane, migration through the surrounding matrix, proliferation, alignment, differentiation into tube-like structures, and synthesis of a new basement membrane. Vasculogenesis involves recruitment and differentiation of mesenchymal cells into angioblasts, which then differentiate into endothelial cells which then form de novo vessels (see, e.g., Folkman et al (1996) *Cell* 87:1153-5).

Inappropriate, or pathological, angiogenesis is involved in the growth of atherosclerotic plaque, diabetic retinopathy, degenerative maculopathy, retrolental fibroplasia, idiopathic pulmonary fibrosis, acute adult respiratory distress syndrome, and asthma. Furthermore, tumor progression is associated with neovascularization, which provides a mechanism by which nutrients are delivered to the progressively growing tumor tissue.

There is a need in the art for methods of reducing pathological angiogenesis. The present invention addresses this need.

LITERATURE

Schuller et al. (1989) *Carcinogenesis* 10:1753-1755; Maneckjee et al. (1994) *Cell Growth Differ.* 5:1033-1040; Hong et al. (1995) *J. Pharm. Sci.* 84:65-70; Schuller et al. (1989) *Biochem. Pharmacol.* 38:3439-3442; U.S. Pat. No. 5,318,957; Yancopoulos et al. (1998) *Cell* 93:661-4; Folkman et al. (1996) *Cell* 87; 1153-5; and Hanahan et al. (1996) *Cell* 86:353-64). Carmeliet et al. (2000) *Nature* 407:249-257; Folkman (1995) *Nat Med* 1:27-31; Heeschen et al. (2001) *Nat Med* 7:833-837; Grando et al. (1995) *J Invest Dermatol* 105: 774-781; Macklin et al. (1998) *Pharmacol Exp Ther* 287:435-439; Wessler et al. (1999) *Clin Exp Pharmacol Physiol* 26:198-205; Kawashima et al. (1989) *Neurosci Lett* 104:336-339; Kawashima et al. (1990) *Neurosci Lett* 119:156-158; Kureishi et al. (2000) *Nat Med* 6:1004-1010; Jang et al. (2000) *Circulation* 102:1414-1419; Couffinhal et al. (1998) *Am J Pathol* 152:1667-1679; Lagasse and Weissman (1996) *J Immunol Methods* 197:139-150; and Villablanca (1998 *J Appl Physiol* 84:2089-2098.

SUMMARY OF THE INVENTION

The present invention provides methods of reducing angiogenesis in an individual. The methods generally involve administering to the individual an effective amount of a nicotinic acetylcholine receptor antagonist. The methods are useful to treat conditions associated with or resulting from angiogenesis, particularly pathological angiogenesis. The invention further provides methods of treating a condition associated with or resulting from angiogenesis.

FEATURES OF THE INVENTION

The present invention features a method of reducing angiogenesis in a mammal. The method generally involves administering to a mammal a nicotinic acetylcholine receptor (nAChR) antagonist in an amount effective to reduce angiogenesis.

The present invention also features method of treating a disorder associated with pathological angiogenesis. In some embodiments, the invention features a method of inhibiting abnormal fibrovascular growth in a mammal. In some of these embodiments, the abnormal fibrovascular growth is associated with inflammatory arthritis. In some embodiments, the invention features a method of inhibiting a proliferative retinopathy in a mammal. In some of these embodiments, the proliferative retinopathy occurs as a result of diabetes in the mammal. The methods generally involve administering to a mammal an nAChR antagonist in an amount effective to reduce pathological angiogenesis. In some embodiments, the methods further comprise administering a second angiogenesis inhibitor.

The present invention further features a method of inhibiting tumor growth in a mammal. In some embodiments, the invention features a method of inhibiting pathological neovascularization associated with a tumor. The methods generally involve administering to a mammal an nAChR antagonist in an amount effective to reduce angiogenesis associated with a tumor. In some embodiments, the invention further comprises administering an anti-tumor chemotherapeutic agent other than an nAChR antagonist.

Suitable nAChR antagonists for use in the methods of the invention include, but are not limited to, mecamylamine; hexamethonium, dihydro-beta-erythroidine, d-tubocurarine, pempidine, chlorisondamine, erysodine, trimethaphan camsylate, pentolinium, bungarotoxin, succinylcholine, tetraethylammonium, trimethaphan, chlorisondamine, and trimethidinium. The nAChR antagonist can be administered by any route of administration, including, but not limited to, intravenous, in or around a solid tumor, systemic, intraarterial, and topical.

DEFINITIONS

Figure 1:
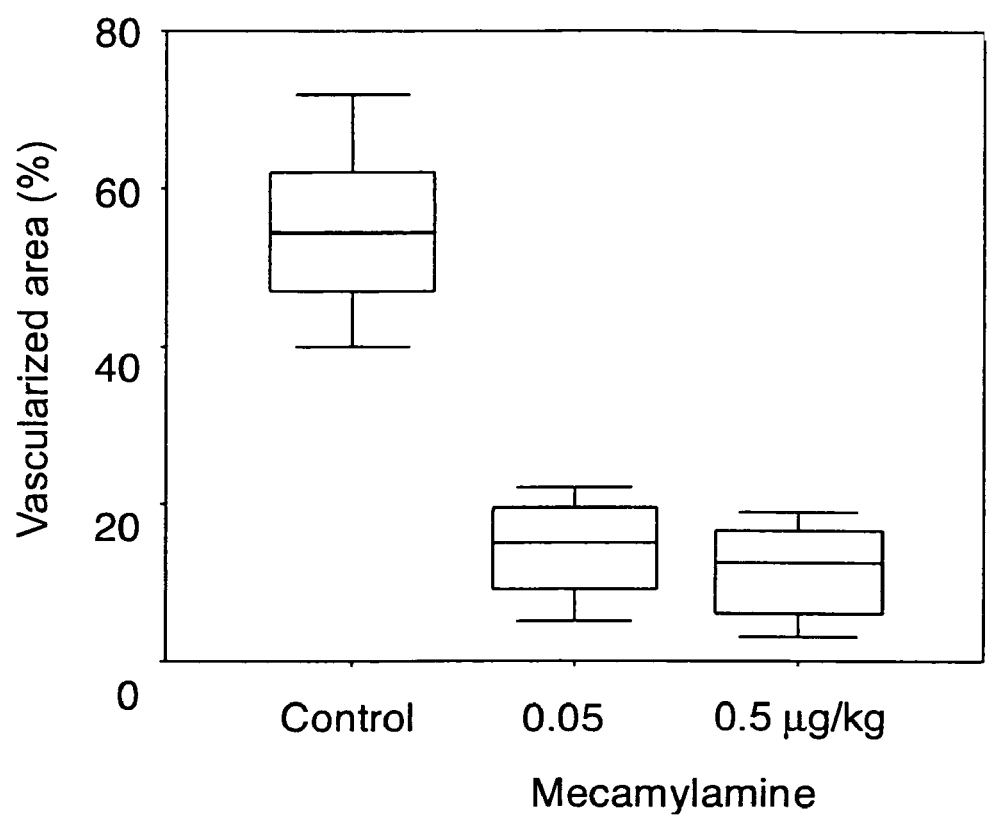
FIG. 1 depicts results with disc angiogenesis system showing that mecamylamine inhibits angiogenesis in vivo.

The terms "nicotinic acetyl choline receptor antagonist," "nicotinic antagonist," and "nicotinergic receptor antagonist" are used interchangeably herein to refer to compounds that substantially specifically bind a nicotinic acetylcholine receptor (nAChR) and provide a pharmacological effect, e.g., reduction of angiogenesis. "Nicotinic acetyl choline receptor antagonist" encompass naturally-occurring compounds (including, but not limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small molecules, peptides, etc.), and pharmaceutically acceptable salts of the foregoing.

The terms "treatment", "treating" and the like are used herein to generally mean obtaining a desired pharmacologic and/or physiologic effect, e.g., reduction of angiogenesis and/or vasculogenesis. The effect may be prophylactic in terms of completely or partially preventing a disease or symptom thereof and/or may be therapeutic in terms of a partial or complete cure for a disease and/or adverse effect attributable to the disease due to endogenous activation of nAChR. "Treatment" as used herein covers any treatment of a disease in a mammal, particularly a human, and includes: (a) preventing a disease or condition from occurring in a subject who may be predisposed to the disease but has not yet been diagnosed as having it; (b) inhibiting the disease, e.g., arresting its development; or (c) relieving the disease. In the context of the present invention, reduction of angiogenesis and/or vasculogenesis is employed for subject having a disease or condition amenable to treatment by reducing angiogenesis.

By "therapeutically effective amount of a nicotinic acetylcholine receptor antagonist" is meant an amount of an nAChR antagonist effective to facilitate a desired therapeutic effect, e.g., a desired reduction of angiogenesis and/or vasculogenesis. The precise desired therapeutic effect will vary according to the condition to be treated.

By "isolated" is meant that the compound is separated from all or some of the components that accompany it in nature.

By "substantially pure nicotinic acetylcholine receptor antagonist" is meant that the nAChR antagonist has been separated from components that accompany it in nature. Typically, an nAChR antagonist is substantially pure when it is at least 60%, by weight, free from naturally-occurring organic molecules with which it is naturally associated. Preferably, the preparation is at least 75%, more preferably at least 90%, and most preferably at least 99%, by weight, nAChR antagonist. A substantially pure nAChR antagonist can be obtained, for example, by extraction from a natural source, by chemically synthesizing the compound, or by a combination of purification and chemical modification. Purity can be measured by any appropriate method, e.g., chromatography, mass spectroscopy, HPLC analysis, etc.

An nAChR antagonist is substantially free of naturally associated components when it is separated from those contaminants which accompany it in its natural state. Thus, e.g., an nAChR antagonist which is chemically synthesized or produced in a cellular system different from the cell from which it naturally originates will be substantially free from its naturally associated components. In many embodiments, e.g., where an nAChR antagonist is chemically synthesized, the nAChR antagonist is generally substantially pure, e.g., at least about 90% pure, at least about 95% pure, or at least about 99% pure.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nicotinic acetylcholine receptor antagonist" includes a plurality of such antagonists and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of reducing angiogenesis in an individual. The methods generally involve administering to an individual an effective amount of a nicotinic acetylcholine receptor (nAChR) antagonist. The methods are useful to treat conditions and disorders associated with or resulting from angiogenesis, particularly pathological angiogenesis.

The invention is based on the observation that there is an endogenous pathway for angiogenesis that is dependent upon cholinergic receptors on endothelial cells. In the absence of nicotine, this pathway contributes substantially to angiogenesis. The following observations were made: 1) inhibition of nAChR significantly and reversibly reduced capillary network formation in vitro; 2) inhibition of nAChR reduced the angiogenic response to inflammation (disc angiogenesis model), ischemia (femoral artery ligation model), and neoplasia (Lewis lung cancer model); 3) ischemia resulted in an increase in nAChR expression. These data reveal for the first time that nAChR are involved in the native angiogenic response. It was found that nAChR antagonists block angiogenesis in tumors, and reduce tumor growth by about 50%.

The results presented herein indicate that nAChR antagonists are useful to treat conditions and disorders associated with and/or resulting from pathological angiogenesis, including, e.g., cancer, atherosclerosis, proliferative retinopathies, excessive fibrovascular proliferation as seen with chronic arthritis, psoriasis, and vascular malformations such as hemangiomas.

Methods of Reducing Angiogenesis

The present invention provides methods of reducing angiogenesis in an individual. The methods generally involve administering to an individual an effective amount of a nicotinic acetylcholine receptor (nAChR) antagonist. Thus, the methods involve reducing angiogenesis by inhibiting an endogenous pathway for angiogenesis that is dependent upon, or mediated by, an nAChR receptor. The endogenous pathway is activated in the absence of nicotine.

Nicotinic Acetylcholine Receptor Antagonists

Any of a variety of nAChR antagonists can be used in the methods of the present invention. Examples include, but are not limited to, mecamylamine; hexamethonium (Wotring et al., 1995 Neuroscience 67: 293-300); dihydro-beta-erythroidine (Stolerman et al., 1997 Psychopharmacology 129: 390-397); d-tubocurarine (Wotring et al., 1995); pempidine (Rapier et al., 1990 J. Neurochem. 54: 937-945); chlorisondamine (Caggiula et al., 1995 Psychopharmacology 122: 301-306); erysodine (Decker et al., 1995 Eur. J. Pharmacol. 280: 79-80); trimethaphan camsylate (Hisayama et al., 1988 Br. J. Pharmacol. 95:465-472); pentolinium; bungarotoxin; succinylcholine; tetraethylammonium; trimethaphan; chlorisondamine; and trimethidinium.

Suitable nAChR antagonists also include modulators of nAChR, including, but not limited to, agents that reduce the level of an nAChR on a cell; and agents that reduce an activity of an nAChR. Analogues of nicotine, such as the substituted pyridines 2-ethylpyridine and 3-ethylpyridine, may also have anti-angiogenic effects.

Nicotinic antagonists may be administered either as a free base, or in the form of a pharmaceutically acceptable salt thereof. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids.

Nicotinic acetylcholine receptor antagonists can be identified using readily available methods, including those described in the Example. The ability of a candidate agent to reduce angiogenesis can be assessed in vitro or in vivo using any known method, including, but not limited to, an in vitro Matrigel assay, a disc angiogenesis system, a murine model of hind limb ischemia, a murine model of lung cancer, and the like.

Pharmaceutical Compositions

Upon reading the present specification, the ordinarily skilled artisan will appreciate that the pharmaceutical compositions comprising an nAChR antagonist described herein can be provided in a wide variety of formulations. More particularly, the nAChR antagonist can be formulated into pharmaceutical compositions by combination with appropriate, pharmaceutically acceptable carriers or diluents, and may be formulated into preparations in solid, semi-solid (e.g., gel), liquid or gaseous forms, such as tablets, capsules, powders, granules, ointments, solutions, suppositories, injections, inhalants and aerosols. Where the nAChR antagonist is a naturally-occurring compound, the pharmaceutical composition can also be provided as an herbal preparation.

The nAChR antagonist formulation used will vary according to the condition or disease to be treated, the route of administration, the amount of nAChR antagonist to be administered, and other variables that will be readily appreciated by the ordinarily skilled artisan. In general, and as discussed in more detail below, administration of nAChR antagonists can be either systemic or local, and can be achieved in various ways, including, but not necessarily limited to, administration by a route that is oral, parenteral, intravenous, intra-arterial, inter-pericardial, intramuscular, intraperitoneal, intra-articular, intra-ocular, topical, transdermal, transcutaneous, subdermal, intradermal, intrapulmonary, etc.

In pharmaceutical dosage forms, the nAChR antagonist may be administered in the form of their pharmaceutically acceptable salts, or they may also be used alone or in appropriate association, as well as in combination, with other pharmaceutically active compounds. The following methods and excipients are merely exemplary and are in no way limiting.

The nAChR antagonist can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Formulations suitable for topical, transcutaneous, and transdermal administration may be similarly prepared through use of appropriate suspending agents, solubilizers, thickening agents, stabilizers, and preservatives. Topical formulations may be also utilized with a means to provide continuous administration of mecamylamine or other nAChR antagonist by, for example, incorporation into slow-release pellets or controlled-release patches.

The nAChR antagonist can also be formulated in a biocompatible gel, which gel can be applied topically or implanted (e.g., to provide for sustained release of nAChR antagonist at an internal treatment site). Suitable gels and methods for formulating a desired compound for delivery using the gel are well known in the art (see, e.g., U.S. Pat. Nos. 5,801,033; 5,827,937; 5,700,848; and MATRIGEL™).

For oral preparations, the nAChR antagonist can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The nAChR antagonist can be utilized in aerosol formulation to be administered via inhalation. The compounds of the present invention can be formulated into pressurized acceptable propellants such as dichlorodifluoromethane, propane, nitrogen and the like.

Furthermore, the nAChR antagonist can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term unit dosage form, as used herein, refers to physically discrete units suitable as unitary dosages for human and/or animal subjects, each unit containing a predetermined quantity of nAChR antagonist calculated in an amount sufficient to produce the desired reduction in angiogenesis in association with a pharmaceutically acceptable diluent, carrier or vehicle. The specifications for the unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an nAChR antagonist is administered in a combination therapy with one or more additional therapeutic agents. Exemplary therapeutic agents include therapeutic agents used to treat cancer, atherosclerosis, proliferative retinopathies, chronic arthritis, psoriasis, hemangiomas, etc.

Dose

The dose of nAChR antagonist administered to a subject, particularly a human, in the context of the present invention should be sufficient to effect a therapeutic reduction in angiogenesis in the subject over a reasonable time frame. The dose will be determined by, among other considerations, the potency of the particular nAChR antagonist employed and the condition of the subject, as well as the body weight of the subject to be treated. For example, the level or affinity or both of the nAChR antagonist for the nicotinic acetylcholine receptor may play a role in regulating the compound's anti-angiogenic activity. The size of the dose also will be determined by the existence, nature, and extent of any adverse side-effects that might accompany the administration of a particular compound.

In determining the effective amount of nAChR antagonist in the reduction of angiogenesis, the route of administration, the kinetics of the release system (e.g., pill, gel or other matrix), and the potency of the nicotine agonist are considered so as to achieve the desired anti-angiogenic effect with minimal adverse side effects. The nAChR antagonist will typically be administered to the subject being treated for a time period ranging from a day to a few weeks, consistent with the clinical condition of the treated subject.

As will be readily apparent to the ordinarily skilled artisan, the dosage is adjusted for nAChR antagonists according to their potency and/or efficacy relative to a standard, e.g., mecamylamine. A dose may be in the range of about 0.01 mg to 10 mg, given 1 to 20 times daily, and can be up to a total daily dose of about 0.1 mg to 100 mg. If applied topically, for the purpose of a systemic effect, the patch or cream would be designed to provide for systemic delivery of a dose in the range of about 0.01 mg to 10 mg. If the purpose of the topical formulation (e.g., cream) is to provide a local anti-angiogenic effect, the dose would likely be in the range of about 0.001 mg to 1 mg. If injected for the purpose of a systemic effect, the matrix in which the nAChR antagonist is administered is designed to provide for a systemic delivery of a dose in the range of about 0.001 mg to 1 mg. If injected for the purpose of a local effect, the matrix is designed to release locally an amount of nAChR antagonist in the range of about 0.003 mg to 1 mg.

The following are non-limiting examples of dosages. For mecamylamine hydrochloride, the oral dose is usually 25 mg daily, but can be as low as 2.5 mg daily. Trimethaphan camsylate is given intravenously in a dosage of 0.1-4.0 mg/minute, and the infusion rate can be increased as deemed necessary by the medical personnel. Pentolinium Tartrate is administered orally or by injection (subcutaneous or intramuscular) at dosages of 20, 40, or 100 mg; or as an injection in 10 ml vials containing 10 mg/ml.

Regardless of the route of administration, the dose of nAChR antagonist can be administered over any appropriate time period, e.g., over the course of 1 to 24 hours, over one to several days, etc. Furthermore, multiple doses can be administered over a selected time period. A suitable dose can be administered in suitable subdoses per day, particularly in a prophylactic regimen. The precise treatment level will be dependent upon the response of the subject being treated.

Combination Therapy

In some embodiments, an nAChR antagonist is administered in a combination therapy with one or more other therapeutic agents, including an inhibitor of angiogenesis; and a cancer chemotherapeutic agent.

Suitable chemotherapeutic agents include, but are not limited to, the alkylating agents, e.g. Cisplatin, Cyclophosphamide, Altretamine; the DNA strand-breakage agents, such as Bleomycin; DNA topoisomerase II inhibitors, including intercalators, such as Amsacrine, Dactinomycin, Daunorubicin, Doxorubicin, Idarubicin, and Mitoxantrone; the nonintercalating topoisomerase II inhibitors such as, Etoposide and Teniposide; the DNA minor groove binder Plicamycin; alkylating agents, including nitrogen mustards such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine; antimetabolites, including folate antagonists such as Methotrexate and trimetrexate; pyrimidine antagonists, such as Fluorouracil, Fluorodeoxyuridine, CB3717, Azacytidine, Cytarabine; Floxuridine purine antagonists including Mercaptopurine, 6-Thioguanine, Fludarabine, Pentostatin; sugar modified analogs include Cyctrabine, Fludarabine; ribonucleotide reductase inhibitors including hydroxyurea; Tubulin interactive agents including Vincristine Vinblastine, and Paclitaxel; adrenal corticosteroids such as Prednisone, Dexamethasone, Methylprednisolone, and Prodnisolone; hormonal blocking agents including estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; and the like.

The nAChR antagonist may be administered with other anti-angiogenic agents. Anti-angiogenic agents include, but are not limited to, angiostatic steroids such as heparin derivatives and glucocorticosteroids; thrombospondin; cytokines such as IL-12; fumagillin and synthetic derivatives thereof, such as AGM 12470; interferon-α; endostatin; soluble growth factor receptors; neutralizing monoclonal antibodies directed against growth factors; and the like.

Reducing Angiogenesis in Vivo

The instant invention provides a method of reducing angiogenesis in a mammal. The method generally involves administering to a mammal an nAChR antagonist in an amount effective to reduce angiogenesis. An effective amount of an nAChR antagonist reduces angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or more, when compared to an untreated (e.g., a placebo-treated) control.

Whether angiogenesis is reduced can be determined using any known method. Methods of determining an effect of an agent on angiogenesis are known in the art and include, but are not limited to, inhibition of neovascularization into implants impregnated with an angiogenic factor; inhibition of blood vessel growth in the cornea or anterior eye chamber; inhibition of endothelial cell proliferation, migration or tube formation in vitro; the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

The invention further provides methods for treating a condition or disorder associated with or resulting from pathological angiogenesis. In the context of cancer therapy, a reduction in angiogenesis according to the methods of the invention effects a reduction in tumor size; and a reduction in tumor metastasis. Whether a reduction in tumor size is achieved can be determined, e.g., by measuring the size of the tumor, using standard imaging techniques. Whether metastasis is reduced can be determined using any known method. Methods to assess the effect of an agent on tumor size are well known, and include imaging techniques such as computerized tomography and magnetic resonance imaging.

Conditions Amenable to Treatment

Any condition or disorder that is associated with or that results from pathological angiogenesis, or that is facilitated by neovascularization (e.g., a tumor that is dependent upon neovascularization), is amenable to treatment with an nAChR antagonist.

Conditions and disorders amenable to treatment include, but are not limited to, cancer; atherosclerosis; proliferative retinopathies such as diabetic retinopathy, age-related maculopathy, retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

Subjects Suitable for Treatment

Subjects suitable for treatment using the methods of the instant invention include a subject who has a condition or disorder described above, e.g., a disorder amenable to treatment by reducing angiogenesis. In some embodiments, the individual does not have a level of nicotine in the subject's body at a level that would stimulate angiogenesis. In some embodiments, the individual is not using a nicotine-containing product, wherein use of such a product would result in the introduction of nicotine into the body of the subject in an amount sufficient to stimulate angiogenesis) concurrently with being administered the nAChR antagonist. Nicotine-containing products include, but are not limited to, tobacco products such as cigarettes, tobacco for smoking pipes, cigars, chewing tobacco, snuff, and tobacco-containing gum and lozenges, or nicotine containing patches or gums.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Nicotine Receptor Antagonists Inhibit Angiogenesis

Methods

In Vitro Matrigel Assay. Human umbilical vein endothelial cells (HUVEC) and human microvascular endothelial cells (HMVEC; up to $5^{th}$ passage; BioWhittaker, Walkersville, Md.) were grown in EGM-MV supplemented with 5% FBS, 0.5 ml hEGF, 0.2 ml hydrocortisone, 2.0 ml BBE, and 0.5 ml GA-1000 (Biowhittaker). Four-well chamber slides were coated with growth factor enhanced Matrigel (Becton Dickinson, Bedford, Mass.) and equilibrated with basal medium. Kureishi et al. (2000) *Nat Med* 6:1004-1010. Cells were seeded on top of the gel at a density of $10^3$ cells/well in fresh basal medium containing 5% FBS. After two hours, increasing concentrations of mecamylamine ($10^{-12}$ to $10^{-4}$ M; Sigma, St. Louis, Mont.) or vehicle were added to the medium. Development of tube formation in the center of each well was investigated at 24, 48, and 72 hours.

Disc Angiogenesis System. A disc of polyvinyl alcohol sponge (Rippey, El Dorado Hills, Calif.), covered with nitrocellulose cell-impermeable filters (Millipore, Burlington, Mass.), allows capillaries to grow only through the rim of the disc. The randomized treatment for the 2-week study period was delivered via osmotic minipumps (0.25 μl/hr; Durect, Cupertino, Calif.). Those discs were subcutaneously implanted in the back of 10-week old C57BL/6J mice or in some experiments in the back of α7-nAChR-deficient (B6.129S7-Chrna7$^{tm1Bay}$) mice (n=6 per group; Jackson, Bar Harbor, Me.). Two weeks later, mice were anaesthetized and infused with space-filling fluorescent microspheres (0.2 μm, Molecular Probes, Eugene, Oreg.) through the left ventricle of the heart. Both the area of the disc covered with perfused vessels and the vessel density were quantified. Heeschen et al. (2001) *Nat Med* 7:833-837; and Jang et al. (2000) *Circulation* 102:1414-1419 (3, 10) The α7-nAChR in growing vessels were identified by immunohistochemistry (Santa Cruz Biotechnology, Santa Cruz, Calif.). To verify the specificity of the staining, discs explanted from homozygous α7-nAChR$^{-/-}$ mice were used as a negative control.

Murine Model of Hind Limb Ischemia. In 10-week old C57BL/6J mice, the distal end of the external iliac artery and the deep and superficial femoral artery were ligated (n=8 animals per group). Mecamylamine was administered for three weeks by daily intramuscular injection. Serum VEGF levels were determined with a mouse VEGF ELISA kit (R&D System, Minneapolis, Minn.). Capillary density was determined in the adductor and semimembranous muscles. In 10 μm cryostat sections, cut transverse to the mid-belly of the muscle, capillaries were identified by monoclonal antibodies against CD31 (BD PharMingen, San Diego, Calif.) and myocytes were counterstained with eosin (Sigma). Capillary density for each section was determined in ten randomly selected fields and is expressed as a ratio of capillaries to myocytes.

FACS. Fluorescence-activated cell sorting was used to identify the cellular population mobilized by ischemia and ischemia plus mecamylamine, respectively. At each time point (baseline, 3, 7, 14 days), blood was obtained from the right atrium. Bone marrow was isolated from bilateral femurs and tibias of each animal and incubated in HBSS (1% FCS) on ice. Peripheral blood and bone marrow cells were incubated with fluorescent-labeled antibodies and analyzed with a FACS-Vantage flow cytometer (Becton Dickinson, Franklin Lakes, N.J.). FITC-conjugated antibody against mouse CD34 and PE-conjugated antibody against mouse Flk-1 (BD PharMingen, San Diego, Calif.) were used as endothelial lineage markers. The analysis of CD34+ and Flk-1+ cells was performed after gating for monocyte size. Biotinylated antibodies against MAC-1 (BD PharMingen) conjugated to Avidin-Texas Red (BD PharMingen) were used as a monocyte/macrophage lineage marker after gating for monocyte cell size with the exclusion of granulocytes that were marked by Ly-6G GR-1 against mouse conjugated to APC (BD PharMingen). Lagasse et al. (1996) *J Immunol Methods* 197:139-150. Staining was performed in the presence of saturating concentrations of rat monoclonal unconjugated antibodies against Fc receptors (anti-CD16/32, BD PharMingen) to reduce nonspecific binding. Dead cells were excluded by propidium iodide staining and erythrocytes were excluded by light scatter gating. Each analysis included 100,000 events. Data were analyzed using FloJo software (Becton Dickinson).

Lewis Lung Tumor Model. A total of $10^6$ Lewis lung carcinoma cells (ATCC, Manassas, Va.) were cultured in RPMI 1640 supplemented with 10% FBS. Cancer cells were subcutaneously injected into each flank or orthotopically introduced into the lung parenchyma via a limited skin incision without thoracotomy of 10-week old C57BL/6J wild type mice. Animals received mecamylamine (3 mg/kg) or vehicle via osmotic mini pumps. Mice injected subcutaneously with tumor cells were checked on a daily basis for the presence of a palpable tumor and tumor growth was measured with a guage. Tumor size was calculated as the product of length×width×0.5 cm³. When mice in any group were bearing tumors >1.5 cm³, the experiment was stopped and all animals sacrificed for histological evaluation. Tumor vessels were identified by infusion of space-filling fluorescent microspheres (0.2 μm; Molecular Probes) via the left ventricle of the heart.

Statistical Analysis. All results for continuous variables are expressed as medians with 95% confidence intervals (Figures: 75 and 95% CI). Comparisons between groups were analyzed by t test (two-sided) or ANOVA for experiments with more than two subgroups. Post hoc range tests and pair wise multiple comparisons were performed with the t test (two-sided) with Bonferroni adjustment. Comparison of categorical variables was generated by the Pearson $\chi^2$ test. All analyses were performed with SPSS 10.0 (SPSS Inc.). P values <0.05 were considered statistically significant.

Results

In vitro Matrigel Assay

We studied critical steps in angiogenesis, such as migration and differentiation, using an in vitro model of angiogenesis with ECs forming a network of capillary-like structures. After seeding the cells on growth factor-enriched matrigel, HMVECs and HUVECs, respectively, manifested tube formation within 48 hours in response to control medium. However, when the medium was supplemented with increasing concentrations of mecamylamine ($10^{-4}$ to $10^{-12}$ M), a specific non-competitive inhibitor of the nAChR, network formation was inhibited. If mecamylamine treatment ($10^{-6}$ M) was stopped after 36 hours, ECs were still capable of arranging in network-like structures at 72 hours indicating that the effect of mecamylamine was reversible.

Disc Angiogenesis System

To determine if the nAChR are involved in the native angiogenesic response in vivo, we used the disc angiogenesis system. In the control group, 54.9% (95% CI 46.1-63.6) of the cross-sectional area of the disc was covered with new vessels when the disc was removed three weeks after subcutaneous implantation. FIG. 1. Systemic treatment with mecamylamine via osmotic minipumps significantly decreased neovascularization of the disc (14.3% (95% CI 9.0-19.5); P<0.001) FIG. 1. Similarly, when we added hexamethonium, a non-competitive inhibitor of the nAChR that, in contrast to mecamylamine, does not cross the blood-brain-border, neovascularization of the discs was also significantly reduced (11.5% (95% CI 6.5-16.5); P<0.001). Immunohistochemistry for α7-nAChR demonstrated positive staining in the growing vessels in the disc.

Figure 2:
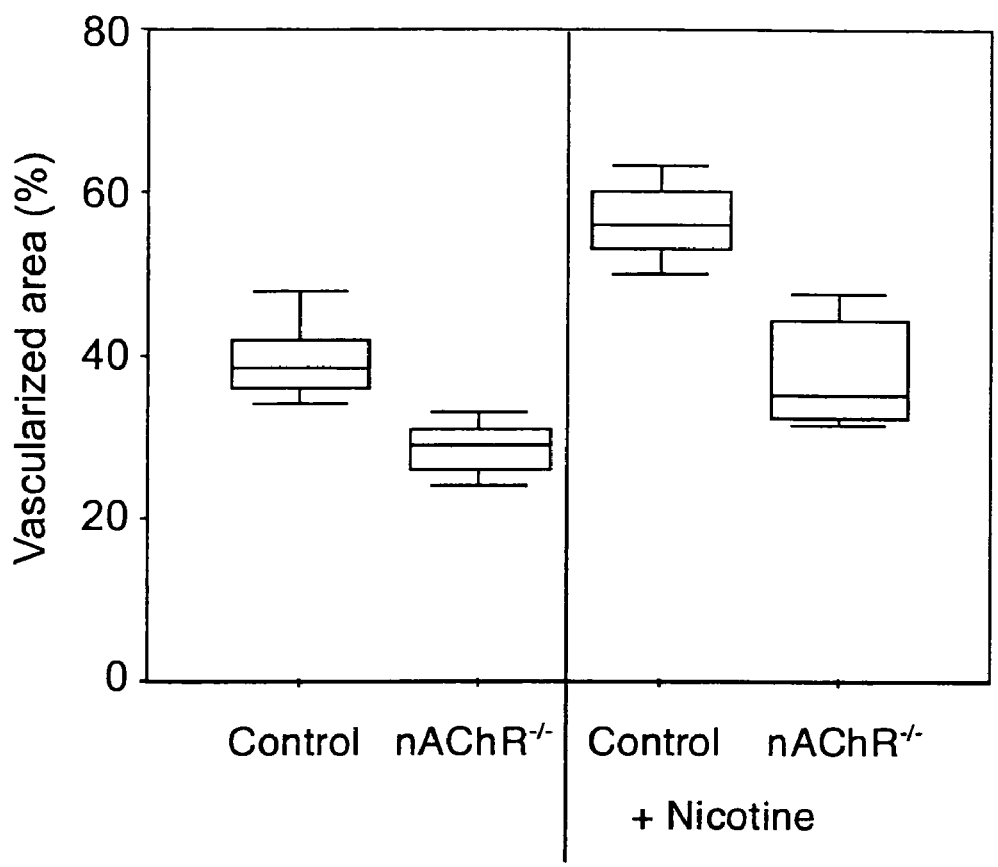
FIG. 2 depicts results showing that in α7 nAChR-deficient mice, the angiogenic response was significantly reduced.

In homozygous α7-nAChR$^{-/-}$ mice, the native angiogenic response was reduced from 39.5 (95% CI 28.7-44.8) for the α7-nAChR$^{+/+}$ wild type to 28.7 mm$^2$ (95% CI 25.2-32.2) (P=0.009) (FIG. 2).

Murine Model of Hind Limb Ischemia

Figure 3:
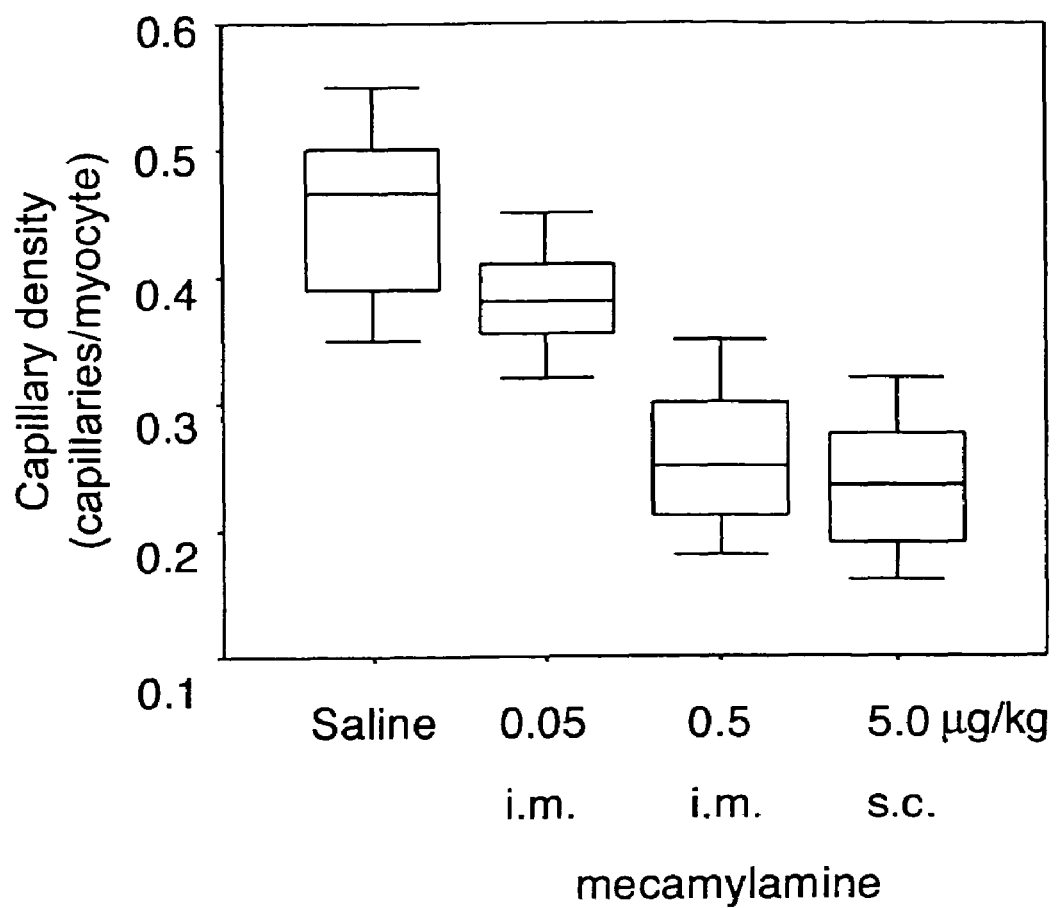
FIG. 3 depicts results with a murine model of hind limb ischemia, showing that as compared to control, mecamylamine decreased capillary density in a dose-dependent fashion.

To determine if nAChR play an important role in the setting of angiogenesis in response to ischemia, we employed the murine model of hind limb ischemia. After unilateral ligation of the superficial and deep femoral artery, we administered mecamylamine or vehicle by intramuscular injections into the ischemic hind limb on a daily basis for a period of three weeks. Animals (each group n=8) received 0, 0.05, or 0.5 µg/kg of mecamylamine. After 3 weeks of treatment, 0.5 µg/kg mecamylamine significantly reduced the angiogenic response from 0.45 capillaries/myocyte (95% CI 0.39-0.51) to 0.26 capillaries/myocyte (95% CI 0.21-0.31) (P<0.001) (FIG. 3). We achieved similar results when we administered mecamylamine systemically via osmotic minipumps (5.0 µg/kg; 0.24 (95% CI 0.19-0.28); P<0.001).

An increase in capillary density does not necessarily change local blood flow without a concomitant increase in collateral vessels. Accordingly, we identified collaterals by double staining for CD31 (ECs) and α-actin (SMCs) using confocal microscopy. The number of collaterals was quantified on cross-sections by identifying vascular lumen lined by CD31-positive endothelium, that were coated by an actin-positive vascular smooth muscle wall, with vessel diameters of at least 0.02 mm. Compared to the non-ischemic hind limb, the number of collateral vessels in the ischemic limb of the control animals significantly increased from 2.6 (95% CI 2.5-4.3) to 7.5 (95% CI 5.2-9.5); (P<0.001) and the median size of the collateral vessels increased from 0.05 mm (95% CI 0.02-0.11) to 0.12 mm (95% CI 0.08-0.15); (P<0.001). Treatment with mecamylamine did not significantly decrease the number of collateral vessels (high dose: 6.2 (95% CI 3.9-8.6); low dose: 7.1 (95% CI 4.7-8.5); P=0.08). However, the median diameter of the vessels significantly decreased to 0.07 mm (95% CI 0.04-0.10) and 0.09 mm (95% CI 0.06-0.11), respectively (P=0.002).

Figure 4:
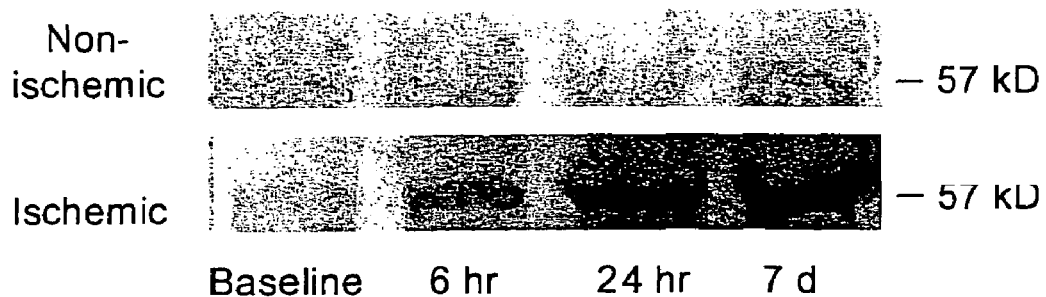
FIG. 4 depicts Western blot analyses demonstrating upregulation of the α7-subunit within 6 hours after onset of ischemia and a maximal effect at 7 days.

Immunohistochemistry for the α7-nAChR demonstrated that this receptor subunit is not expressed at detectable levels in non-ischemic hind limbs. In contrast, 7 days after induction of ischemia, this receptor subtype clearly co-localized with some of the endothelial cells, as identified by von Willebrand factor or CD31, respectively. The upregulated expression of the α7-subunit in ischemic tissue was confirmed by western blot analysis (FIG. 4). The α7-subunit was undetectable at baseline but only 6 hours after induction of hind limb ischemia this receptor subtype was significantly upregulated with a maximal signal at 7 days.

At 7 and 14 days after ligation of the deep and superficial femoral artery, ischemia alone resulted in significant increases in bone marrow CD34$^+$/Flk-1$^+$ cells as compared to baseline (Table 1). Table 1 presents the data, expressed as percentage of endothelial progenitor cells in bone marrow (BM) and peripheral blood (PB) before and after ligation of the femoral artery in the murine model of hind limb ischemia.

TABLE 1

|  |  | Ischemia | Ischemia + mecamylamine | P value |
|---|---|---|---|---|
| Baseline | BM | 0.24 [0.21-0.27] | 0.23 [0.20-0.27] | 0.86 |
|  | PB | 0.05 [0.03-0.07] | 0.06 [0.03-0.08] | 0.69 |
| Day 3 | BM | 1.76 [1.58-1.94] | 1.59 [1.39-1.80] | 0.15 |
|  | PB | 0.34 [0.26-0.43] | 0.33 [0.25-0.41] | 0.85 |
| Day 7 | BM | 4.05 [3.46-4.64] | 3.24 [2.68-3.81] | 0.030 |
|  | PB | 0.43 [0.31-0.54] | 0.38 [0.27-0.49] | 0.48 |
| Day 14 | BM | 5.09 [4.52-5.55] | 3.64 [3.15-4.12] | 0.001 |
|  | PB | 0.51 [0.43-0.59] | 0.44 [0.37-0.50] | 0.084 |

Mobilization of CD34$^+$/Flk-1$^+$ cells into the peripheral blood was simultaneous relative to bone marrow with a significant increase at 7 days and 14 days. Systemic administration of mecarnylamine reduced the number of CD34$^+$/Flk-1$^+$ cells in the bone marrow.

Murine Model of Lung Cancer

Figure 5:
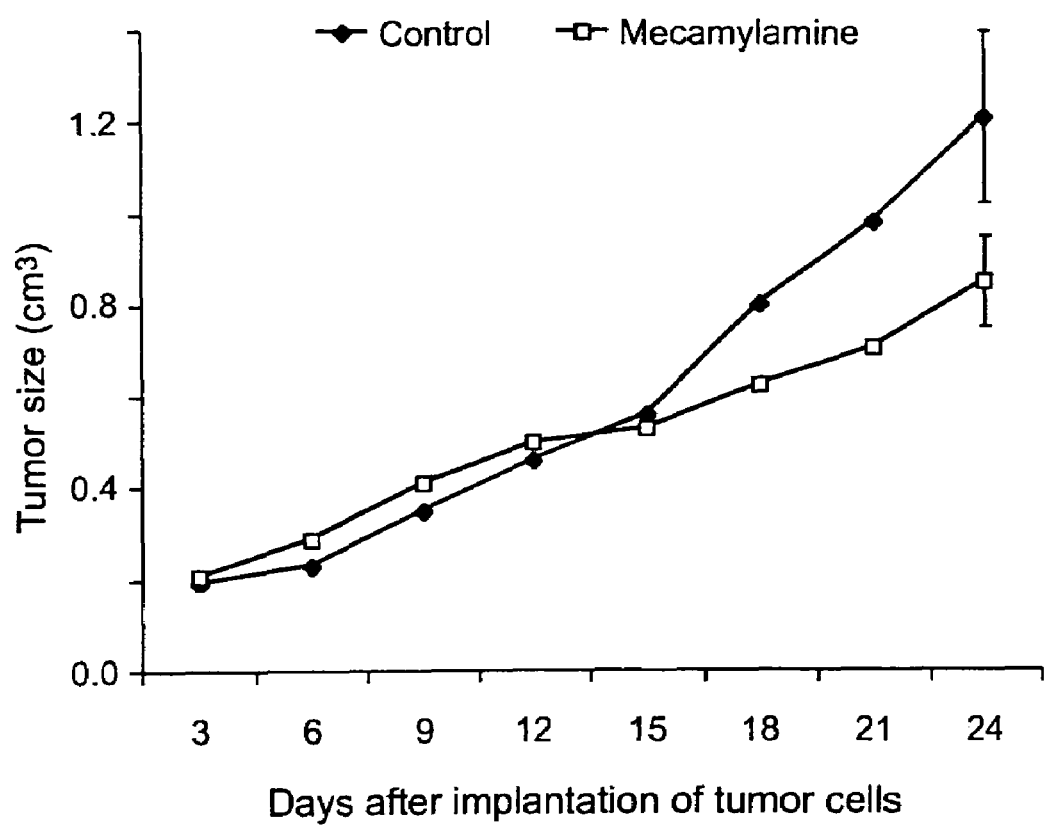
FIG. 5 depicts results with Lewis Lung tumor model: mecamylamine inhibits advanced tumor growth, showing that mecamylamine treated animals showed significantly less tumor growth.

The previous studies indicate that nAChR play an important role in angiogenesis in a broad spectrum of experimental conditions. To determine if mecamylamine could influence tumor angiogenesis, we used the in vivo Lewis lung cancer model. Up to 12 days after implantation of the cancer cells and treatment with vehicle or mecamylamine, all mice exhibited similar tumor size (0.46 cm$^2$ (95% CI 0.32-0.56) versus 0.49 cm$^2$ (95% CI 0.35-0.62); P-0.54) (FIG. 5). At 21-day follow-up, however, tumor growth in the control group significantly exceeded that observed in the mecamylamine group and required sacrifice of the animals (1.21 cm$^3$ (95% CI 0.82-1.36) versus 0.85 cm$^3$ (95% CI 0.66-1.05); P<0.001). This late decrease in tumor growth in the mecamylamine group corresponded with a reduced vascularization of the tumor tissue. We observed a significantly lower capillary density for the mecamylamine group (0.82 capillaries/mm$^2$ (95% CI 0.67-1.22) versus 0.56 capillaries/mm$^2$ (95% CI 0.38-0.92); P<0.001). In another experiment, we orthotopically implanted Lewis lung cancer cells into the lung parenchyma. Larger tumors in the control group required discontinuation of the experiment after 17 days (tumor volume of 0.62 cm$^3$ (95% CI 0.37-0.85) versus 0.45 cm$^3$ (95% CI 0.28-0.66); P<0.001). Again, tumor vascularization was significantly lower in the mecamylamine group (1.56 capillaries/mm$^2$ (95% CI 0.82-2.17) versus 0.98 capillaries/mm$^2$ (95% CI 068-1.31); P<0.001). Furthermore, the systemic levels of VEGF were significantly higher in the control group as compared to the mecamylamine group (152.2 pg/ml (95% CI 98.5-187.2) versus 78.7 pg/ml (95% CI 45.3-99.4)); P<0.001).

In subsequent cell culture experiments, we investigated whether this reduced tumor growth may also be related to a direct anti-proliferative effect of mecamylamine on the cancer cells. After up to 48 hours of treatment with mecamylamine, we did not observe a significant change in the number of Lewis lung cancer cells. We also investigated the effects of increasing mecamylamine concentrations on the percentage of cells undergoing apoptosis during hypoxia using flow cytometry. Again, no difference was observed between the mecamylamine and the control group. Cells that were treated with $10^{-6}$ M mecamylamine during hypoxia were positive for Annexin V in 12% (95% CI 8-15) as compared to 13% (95% CI 10-17) for control cells (P=0.42).

The salient findings of our studies are that: 1) inhibition of nAChR significantly and reversibly reduced capillary network formation in vitro; 2) inhibition of nAChR reduced the angiogenic response to inflammation (disc angiogenesis model), ischemia (femoral artery ligation model), and neoplasia (Lewis lung cancer model); 3) ischemia resulted in an increase nAChR expression. These data reveal for the first time that nAChR are involved in the native angiogenic response.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A method of treating a disorder associated with pathological angiogenesis in a mammal, the method comprising administering to a mammal having a disorder associated with pathological angiogenesis mecamylamine or a pharmaceutically acceptable salt thereof in an amount effective to reduce pathological angiogenesis.

2. The method of claim 1, wherein the disorder is an ocular disease.

3. The method of claim 2, wherein said ocular disease is selected from diabetic retinopathy, retinopathy of prematurity, corneal graft rejection, retrolental fibroplasia, neovascular glaucoma, rubeosis, and macular degeneration.

4. The method of claim 3, wherein the ocular disease is corneal graft rejection.

5. The method of claim 3, wherein said ocular disease is macular degeneration.

6. The method of claim 3, wherein said ocular disease is neovascular glaucoma.

7. The method of claim 3, wherein said ocular disease is retinopathy of prematurity.

8. The method of claim 2, wherein the ocular disease is a proliferative retinopathy.

9. The method of claim 2, wherein the ocular disease is age-related maculopathy, retrolental fibroplasia, or diabetic retinopathy.

10. The method of claim 1, wherein the disorder is rheumatoid arthritis.

11. The method of claim 1, wherein the disorder is psoriasis.

12. The method of claim 1, wherein the disorder is a cancer.

13. The method of claim 12, wherein the cancer is a colon carcinoma.

14. The method of claim 12, wherein the cancer is a lung carcinoma.

15. The method of claim 12, wherein the cancer is a carcinoma of the rectum.

16. The method of claim 12, wherein the cancer is a kidney carcinoma.

17. The method of claim 12, wherein the cancer is a breast carcinoma.

18. The method of claim 12, further comprising administering at least one additional cancer chemotherapeutic agent.

19. The method of claim 18, wherein the at least one additional cancer chemotherapeutic agent is an alkylating agent.

20. The method of claim 18, wherein the at least one additional cancer chemotherapeutic agent is 5-fluorouracil.

21. The method of claim 1, wherein the disorder is atherosclerosis.

22. The method of claim 1, wherein the mammal is a human.

23. The method of claim 1, further comprising administering at least one additional anti-angiogenic agent.

24. The method of claim 23, where the anti-angiogenic agent is a neutralizing monoclonal antibody directed against a growth factor.

25. The method of claim 2, further comprising administering at least one additional anti-angiogenic agent.

26. The method of claim 25, where the anti-angiogenic agent is a neutralizing monoclonal antibody directed against a growth factor.

27. The method of claim 1, wherein the mecamylamine is a free base.

28. The method of claim 1, wherein the mecamylamine is administered as a pharmaceutically acceptable salt.

29. A method of treating an ocular disease associated with pathological angiogenesis, the method comprising administering to a mammal having an ocular disease associated with pathological angiogenesis a nicotinic acetylcholine receptor (nAChR) antagonist or a pharmaceutically acceptable salt thereof in an amount effective to treat the ocular disease, wherein the nAChR antagonist is not tetraethylammonium.

30. The method of claim 29, wherein said ocular disease is selected from diabetic retinopathy, retinopathy of prematurity, corneal graft rejection, retrolental fibroplasia, neovascular glaucoma, rubeosis, and macular degeneration.

31. The method of claim 29, wherein the ocular disease is retinopathy of prematurity.

32. The method of claim 29, wherein said ocular disease is macular degeneration.

33. The method of claim 29, wherein the ocular disease is diabetic retinopathy.

34. The method of claim 29, wherein the nAChR antagonist is selected from the group consisting of mecamylamine; hexamethonium, dihydro-beta-erythroidine, d-tubocurarine, pempidine, chlorisondamine, erysodine, trimethaphan camsylate, pentolinium, bungarotoxin, succinylcholine, trimethaphan, chlorisondamine, and trimethidinium.

35. The method of claim 29, wherein the nAChR antagonist is a free base.

36. The method of claim 29, wherein the nAChR antagonist is administered as a pharmaceutically acceptable salt.

37. The method of claim 29, wherein the nAChR antagonist is hexamethonium.

38. The method of claim 29, wherein the mammal is a human.

39. The method of claim 29, further comprising administering at least one additional anti-angiogenic agent.

40. The method of claim 39, where the anti-angiogenic agent is a neutralizing monoclonal antibody directed against a growth factor.

41. A method of treating psoriasis in a mammal having psoriasis, the method comprising administering to the mammal having psoriasis a nicotinic acetylcholine receptor (nAChR) antagonist or a pharmaceutically acceptable salt thereof in an amount effective to treat the psoriasis.

42. The method of claim 41, wherein the nAChR antagonist is selected from mecamylamine; hexamethonium, dihydro-beta-erythroidine, d-tubocurarine, pempidine, chlorisondamine, erysodine, trimethaphan camsylate, pentolinium, bungarotoxin, succinylcholine, tetraethylammonium, trimethaphan, chlorisondamine, and trimethidinium.

43. The method of claim 41, wherein the nAChR antagonist is hexamethonium.

44. The method of claim 41, further comprising administering at least one additional anti-angiogenic agent.

45. The method of claim 41, wherein the mammal is a human.

46. The method of claim 41, wherein the nAChR antagonist is a free base.

47. The method of claim 41, wherein the nAChR antagonist is administered as a pharmaceutically acceptable salt.

48. The method of claim 41, further comprising administering at least one additional anti-angiogenic agent.

49. The method of claim 48, where the anti-angiogenic agent is a neutralizing monoclonal antibody directed against a growth factor.

* * * * *

UNITED STATES PATENT AND TRADEMARK OFFICE
CERTIFICATE OF CORRECTION

PATENT NO.         : 7,390,821 B2                                  Page 1 of 1
APPLICATION NO.    : 11/366163
DATED              : June 24, 2008
INVENTOR(S)        : John Cooke et al.

It is certified that error appears in the above-identified patent and that said Letters Patent is hereby corrected as shown below:

Col. 1, line 15, please replace the Statement as to Federally Sponsored Research with the following:

Statement As To Federally Sponsored Research

"This invention was made with government support under grant nos. R01 HL-58638 awarded by the National Heart, Lung and Blood Institute, and the Tobacco-Related Research Disease Program of the State of California. The government may have certain rights in this invention." to read:

Statement As To Federally Sponsored Research

-- This invention was made with Government support under contract CA098303 awarded by the National Institutes of Health. The Government has certain rights in this invention. --

Signed and Sealed this

Twenty-fourth Day of November, 2009

David J. Kappos
*Director of the United States Patent and Trademark Office*